United States Patent
Gohno et al.

(10) Patent No.: US 6,616,278 B2
(45) Date of Patent: Sep. 9, 2003

(54) CARRYING CASE AND EYE EXAMINATION DEVICE PROVIDED WITH THE CARRYING CASE

(75) Inventors: Mitsuhiro Gohno, Toyokawa (JP); Mikio Kurachi, Hazu-gun (JP); Naoki Isogai, Nishio (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/938,676

(22) Filed: Aug. 27, 2001

(65) Prior Publication Data

US 2002/0027639 A1 Mar. 7, 2002

(30) Foreign Application Priority Data

Sep. 5, 2000 (JP) ........................................ 2000-273557

(51) Int. Cl.7 ................................................. A61B 3/00
(52) U.S. Cl. ........................................ 351/245; 351/244
(58) Field of Search .................................. 351/200–245

(56) References Cited

U.S. PATENT DOCUMENTS

| 3,637,070 A | 1/1972 | Friedman |
| 4,165,924 A | 8/1979 | Mohrman |
| 5,488,443 A * | 1/1996 | Ota et al. .................... 351/221 |
| 5,528,323 A | 6/1996 | Fujieda et al. |
| 6,056,404 A | 5/2000 | Kawai et al. |
| 6,286,960 B1 * | 9/2001 | Tomita ........................ 351/245 |

FOREIGN PATENT DOCUMENTS

| GB | 897 117 A | 5/1962 |
| JP | A 8-299272 | 11/1996 |
| JP | A 2000-279382 | 10/2000 |

OTHER PUBLICATIONS

U.S. patent application Ser. No. 09/536,471, Tomita, filed Mar. 28, 2000.

* cited by examiner

Primary Examiner—Marvin M. Lateef
Assistant Examiner—John R. Sanders

(57) ABSTRACT

An eye examination device includes an eye examination unit for examining or measuring an eye of an examinee; a carrying case including a first housing part for housing the eye examination unit and a base part which mounts thereon the eye examination unit; a horizontal movement unit which moves the eye examination unit in a horizontal direction with respect to the base part; and a vertical movement unit which moves the eye examination unit in a vertical direction with respect to the base part.

12 Claims, 8 Drawing Sheets

CARRYING CASE AND EYE EXAMINATION DEVICE PROVIDED WITH THE CARRYING CASE

BACKGROUND OF THE INVENTION

1. Field of the Invention

The present invention relates to a carrying case for housing an eye examination unit, and an eye examination device provided with the carrying case.

2. Description of Related Art

An eye examination device of a stationary type which is used in ophthalmological clinics or optician's shops is integrally provided therein with a moving system for moving an eye examination unit including an eye examination optical system, and it is therefore relatively large in size. At the time of making a group ophthalmic examination or an outside sale of spectacles, such a large device is inappropriate to carry in a state that it is housed in a carrying case.

In recent years, eye examination compact devices of a hand-held type easy to carry have been developed for commercial use. The examination or measurement using this type of devices tends to become unstable. This device therefore needs a base or stand for moving an eye examination unit on a horizontal plane as with the stationary type device.

However, the base or stand is bulky if carried separately from the device, while a large-sized carrying case is required if the base is housed together with the device in the carrying case. This results in an increase in weight, which causes the difficulty for a user in carrying by himself the large-sized case housing the device and the base together.

Furthermore, the device of the hand-held type is generally constructed such that a printer and an AC power source are provided as separate units. In the case where those units are housed together with the device in a carrying case for carry, there are problems in housing space, troublesome works of putting in/out or setting up the units.

SUMMARY OF THE INVENTION

The present invention has been made in view of the above circumstances and has an object to overcome the above problems and to provide an eye examination device and a carrying case with excellent usability and with a reduced size and weight appropriate for carry.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an eye examination device including: an eye examination unit for examining or measuring an eye of an examinee; a carrying case including a first housing part for housing the eye examination unit and a base part which mounts thereon the eye examination unit; a horizontal movement unit which moves the eye examination unit in a horizontal direction with respect to the base part; and a vertical movement unit which moves the eye examination unit in a vertical direction with respect to the base part.

According to another aspect of the present invention, there is provided an eye examination device including: an eye examination unit for examining or measuring an eye of an examinee; a support unit which supports the examinee's eye in a stable position; and a carrying case including a first housing part for housing the eye examination unit and a second housing part for housing the support unit, the carrying case further including a base part provided with a movable support part which detachably supports the eye examination unit, a horizontal movement unit which moves the movable support part in a horizontal direction, and a fixed support part which detachably supports the support unit.

Furthermore, according to another aspect of the present invention, there is provided a carrying case for housing an eye examination unit for examining or measuring an eye of an examinee, the carrying case including: a first housing part for housing the eye examination unit; and a base part provided with a movable support part which detachably supports the eye examination unit and a horizontal movement unit which moves the movable support part in a horizontal direction.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
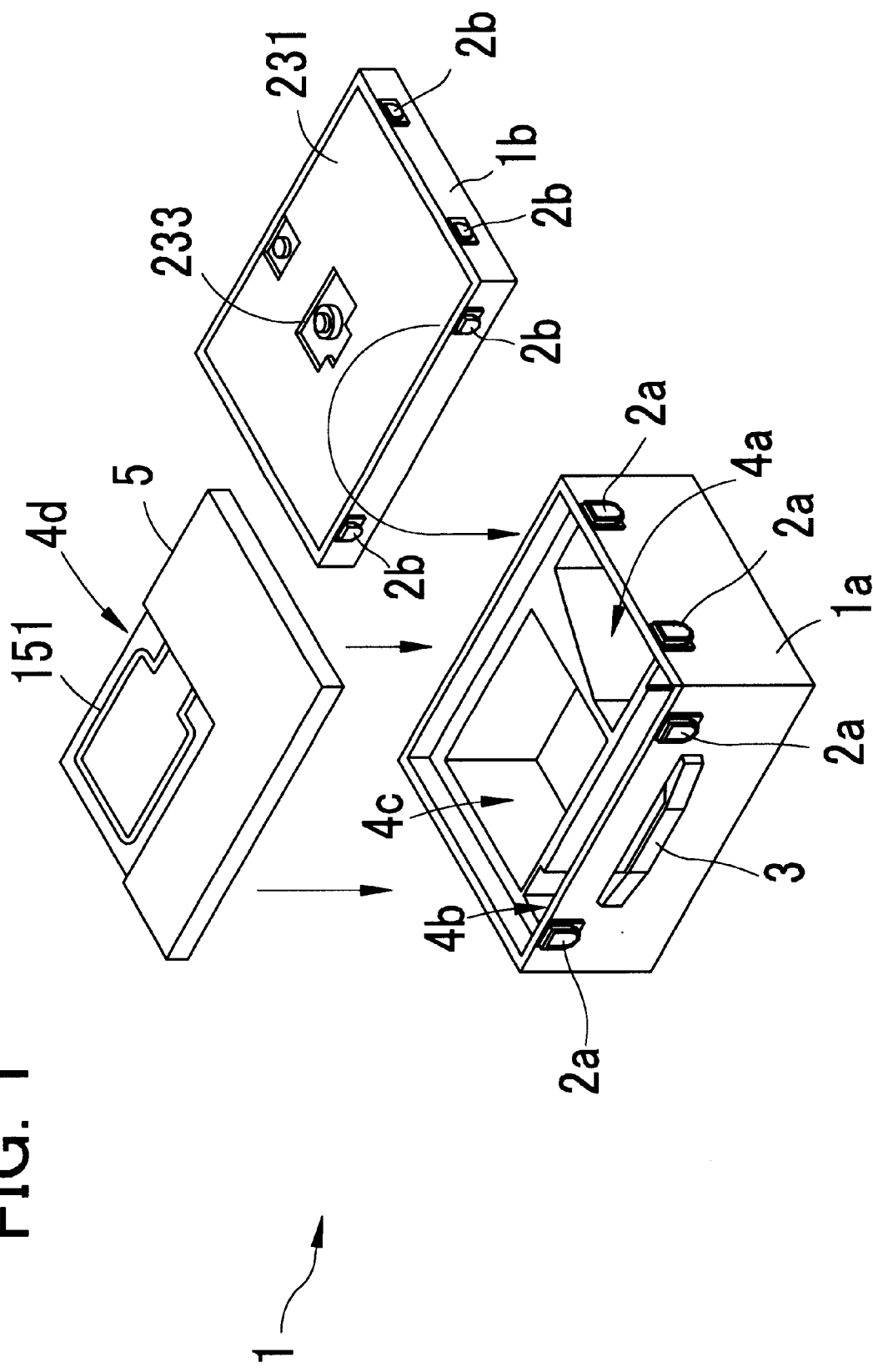
FIG. 1 is a schematic perspective view of a carrying case in an embodiment according to the present invention.
Figure 2:
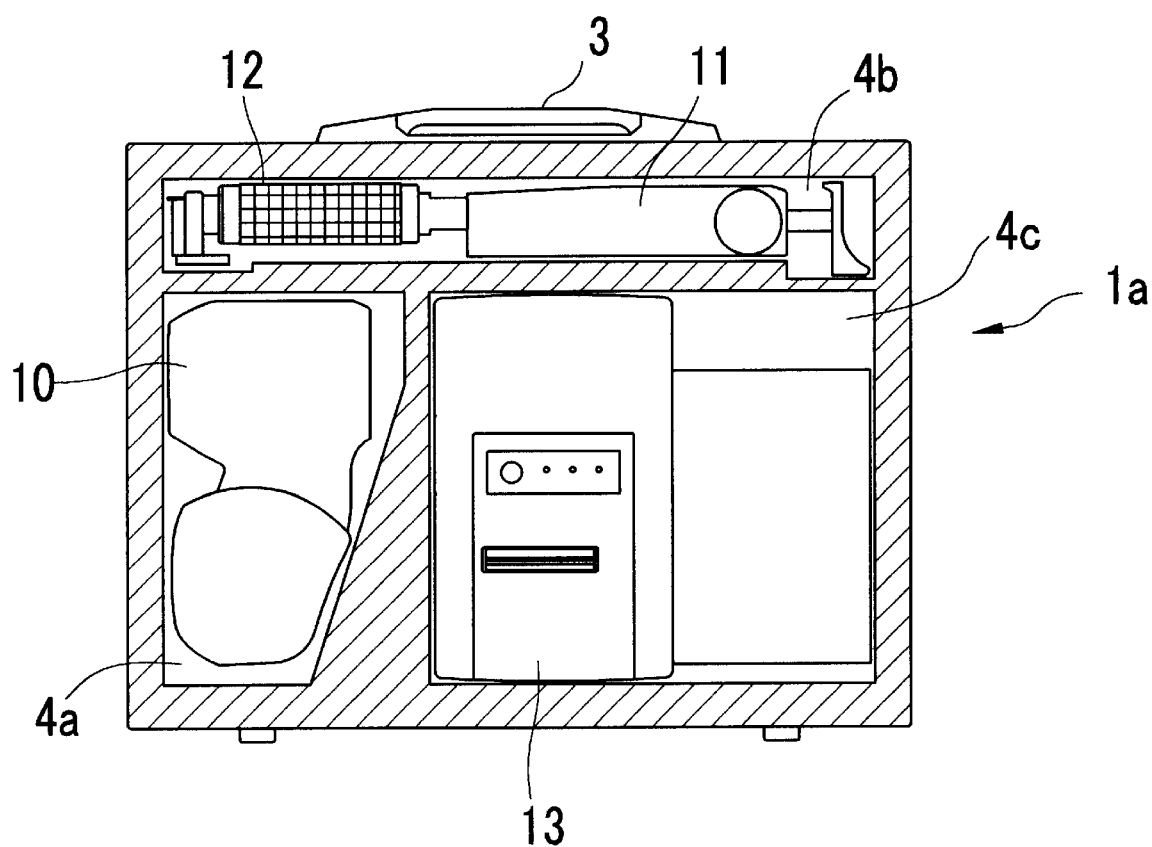
FIG. 2 is a partial section view of showing the carrying case which houses the units consisting an eye examination device in the present embodiment.

A detailed description of a preferred embodiment of a carrying case and an eye examination device embodying the present invention will now be given referring to the accompanying drawings. FIG. 1 is a perspective view of the carrying case for housing for carry an eye examination unit and its peripheral units. FIG. 2 is a partial section view of the carrying case housing those units.

A carrying case 1 is mainly constructed of a case main body 1a and a case cover 1b. The cover 1b is fixable to and detachable from the case body 1a by means of hook metal fittings 2a provided on the case body 1a and female metal fittings 2*b* provided on the cover 1*b*. The hook fittings 2*a* and the female fittings 2*b* are disposed in a pair at plural points. A handle 3 for carry is fixed to the case body 1*a*.

In the case body 1*a*, partition pads are arranged to define a space 4*a* for housing an eye examination unit (measurement unit) 10 of a hand-held type, a space 4*b* for holding a head support unit 11 and a vertical movement unit 12, and a space 4*c* for housing attachments such as a station unit 13 integrally constructed of a printer, an AC power source, and a charger. As shown in FIG. 1, a center pad 5 which is put between the case body 1*a* and the cover 1*b* is provided with a space 4*d* for housing a forehead rest 151.

Figure 3:
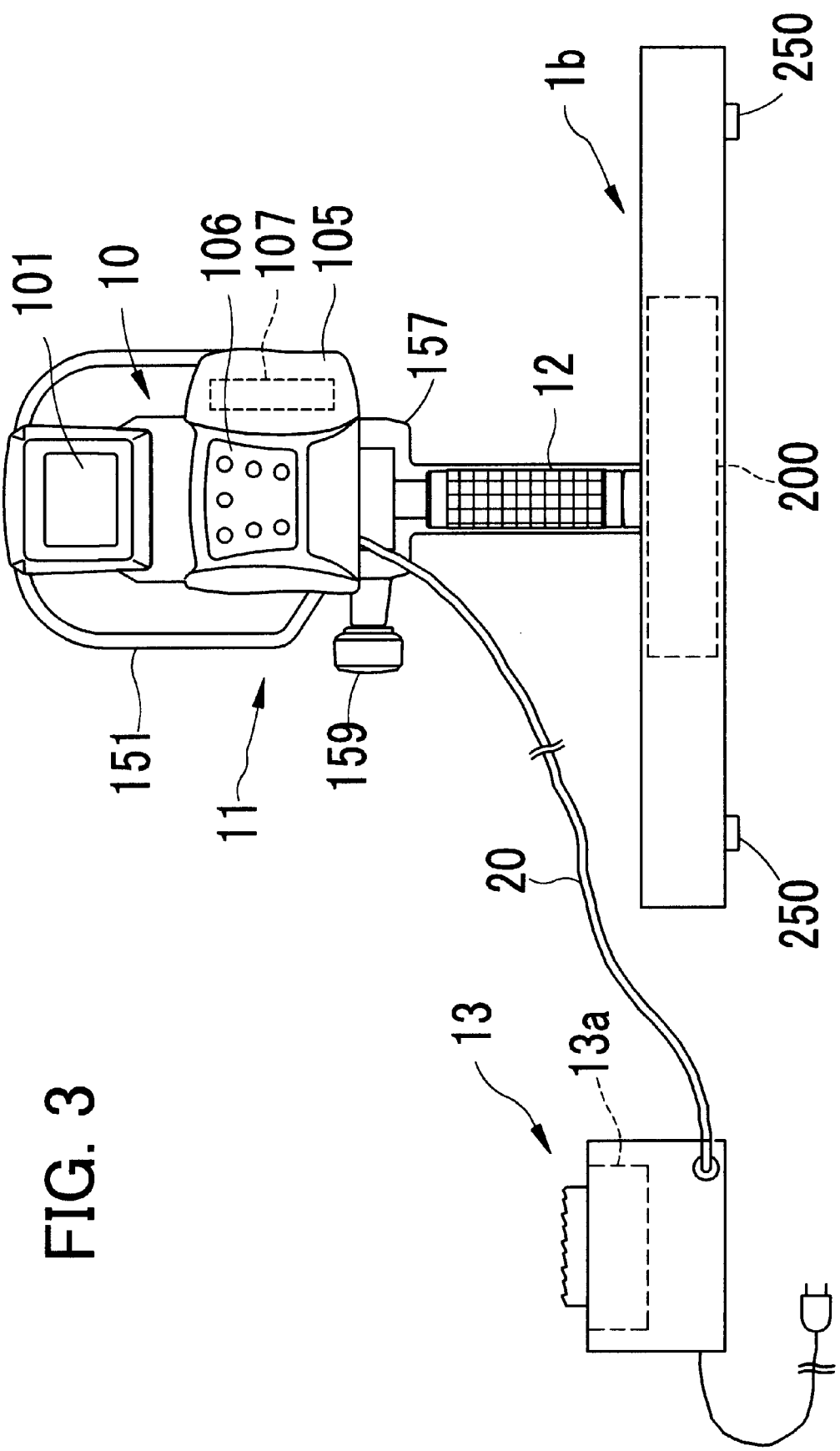
FIG. 3 is a front view of the eye examination device seen from an examiner side, showing a state where an eye examination unit is assembled to be used as a stationary type.
Figure 4:
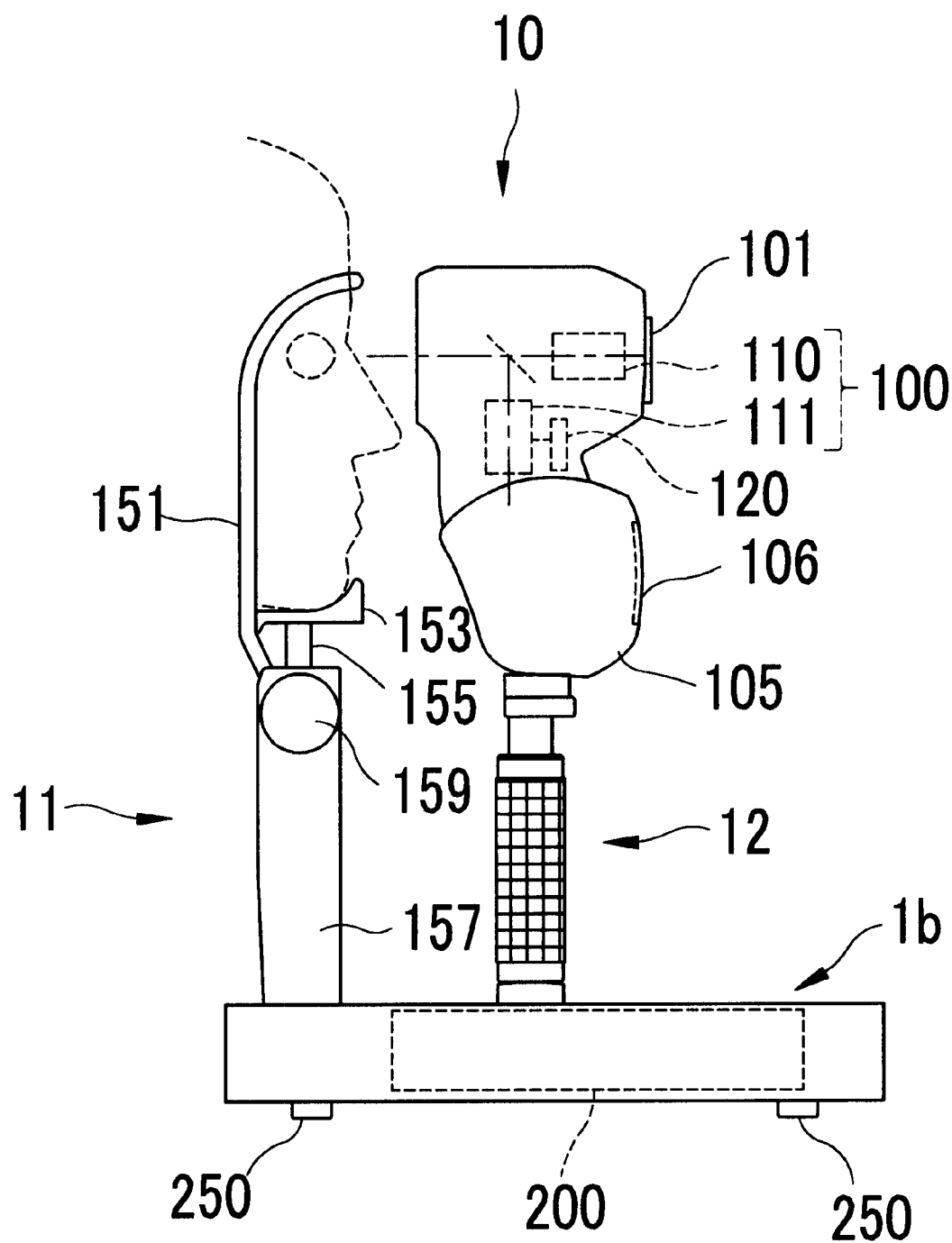
FIG. 4 is a side view of the eye examination device of FIG. 3.

FIGS. 3 and 4 shows the eye examination device assembled such that the eye examination unit 10 is used as a stationary type; FIG. 3 is a front view seen from an examiner side and FIG. 4 is a side view.

The cover 1*b* detached from the case body 1*a* is used as a base of the eye examination unit 10 to be used as a stationary type. At this time, the cover 1*b* is placed so that its inside serves as the upper part of the base, while the outside serves as the bottom part. Four rubber feet 250 are fixed to the outer surface of the cover 1*b*, namely, the bottom part of the base.

The head support unit 11 is detachably mounted on the cover 1*b* on the examinee side. This head support unit 11 is constructed of a forehead rest 151 with curved portions and a vertically movable chin rest 153. This unit 11 is used for supporting an examinee's eye in a stable position. The chin rest 153 is fixed to the top of a vertically movable shaft 155 held by a chin support base 157 so as to be vertically movable. The shaft 155 is vertically moved by rotation of a knob 159 provided on the support base 157. The lower end of the forehead rest 151 is inserted in a hole not shown formed in the upper portion of the base 157. This rest 151 is detachable/attachable with respect to the support base 157.

Figure 5:
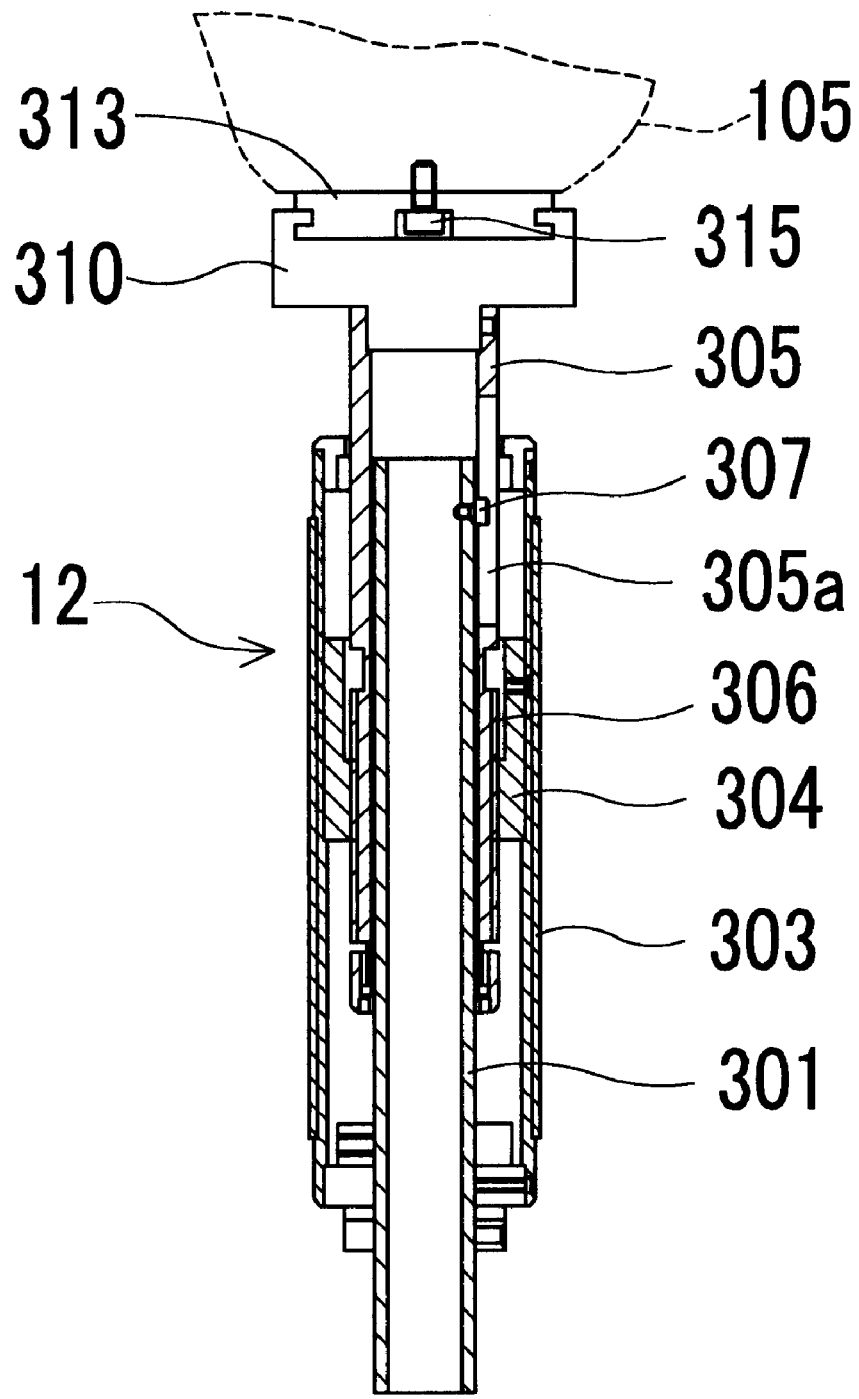
FIG. 5 is a longitudinal section view of a vertical movement system of a vertical movement unit in the present embodiment.

The vertical movement unit 12 which detachably supports the eye examination unit 10 is, as shown in FIG. 5, provided with a knob 303 held rotatably with respect to a support shaft 301, and a vertically movable shaft 305 held vertically movably between the knob 303 and the shaft 301. A male screw 306 formed on the outer periphery of the shaft 305 is configured to engage with a female screw 304 fixed inside the knob 303. By rotation of the knob 303, accordingly, the shaft 305 is vertically moved along the shaft 301. It is to be noted that a pin 307 secured on the shaft 301 is slidably engaged in a vertical slot 305*a* formed on the shaft 305, thereby enabling the shaft 305 to vertically move and disabling the same from rotating.

A mounting holder 310 is fixed to the upper end of the shaft 305. The eye examination unit 10 is detachable/attachable with respect to the holder 310 through a slide base 313. This base 313 is fixable to the eye examination unit 10 by means of a screw 315 which is inserted in a screw hole for a tripod, the screw hole being formed on the underside of a grip part 105 of the eye examination unit 10.

The eye examination unit 10 has a cabinet appropriate to hand hold, which contains an eye examination optical system 100 including a measurement optical system 111 for measuring the eye refractive power of an examinee's eye and an observation optical system 110 for observing the anterior part of the eye. The observation optical system 110 is provided with an optical system which projects an alignment target and an image pickup element which picks up an image of the anterior part of the eye illuminated by light of an illumination light source for the anterior part. The images of the anterior part and the alignment target picked up by the image pickup element are displayed on an LCD monitor 101. The eye refractive power measurement optical system 111 is constructed of a projecting optical system which projects a measurement target to the fundus of the examinee's eye and a light receiving element which detects the image of the target reflected from the eye fundus. The output of the light receiving element is input to a computation control section 120 which thus computes the eye refractive power. It is to be noted that an example of the eye examination optical system 100 is disclosed in U.S. Pat. No. 6,056,404 (corresponding to Japanese patent unexamined publication No. 11-70077) by the same applicant as that of the present invention. The detail thereof is therefore referred to the patent.

The lower portion of the eye examination unit 10 is used as the grip part 105 which is held by hand. On the examiner side of the grip part 105, there is provided an operation section 106 with various switches to be used for eye examination (measurement). The grip part 105 is provided with a built-in buttery source 107, so that the eye examination unit 10 may be used singly as a hand-held type.

The cover 1*b* is provided with a horizontal movement system 200 for horizontally moving the vertical movement unit 12 mounting thereon the eye examination unit 10. The following explanations are made on the structure of the horizontal movement system 200 and the detachment and attachment systems of the head support unit 11 and the vertical movement unit 12, referring to FIGS. 6 and 7.

The horizontal movement system 200 is disposed on a bottom plate 201 secured on the inside of the cover 1*b*. This system 200 is constructed of a lower slidable plate 205 held to be movable forward and backward (i.e., in a direction indicated by an arrow A in FIG. 7) through two slide rails 203 fixed on the bottom plate 201, an upper slidable plate 209 held to be movable leftward and rightward (i.e., in a direction indicated by an arrow B in FIG. 7) through two slide rails 207 mounted on the lower slidable plate 205, and a shaft holder 211 fixedly disposed on the upper slidable plate 209. The holder 211 is formed with a recess 213 which holds the shaft 301 of the vertical movement unit 12 and is fixedly provided with a pin 215. On the other hand, the shaft 301 to be inserted in the recess 213 is formed with a key groove 301*a*. When the shaft 301 is inserted in the holder 211 (the recess 213) so that the groove 301*a* is engaged with the pin 215, the vertical movement unit 12 is attached to the cover 1*b* with a single motion. The shaft 301 is thus disabled from rotating.

The horizontal movement system 200 is also provided with a stopper mechanism. Numeral 221 is a ball catch secured to the bottom plate 201 through an attachment plate 223. A protrusion 225 engageable with the ball catch 221 is fixed to the upper slidable plate 209. When the protrusion 225 is inserted between two rigid balls constituting the ball catch 221, the upper slidable plate 209 is fixed without moving. To release this fixation state of the slidable plate 209, the knob 303 of the vertical movement unit 12 is pushed by the examiner's hand toward the examinee. Thus, the protrusion 225 is disengaged from the ball catch 221, enabling the horizontal movement of the eye examination 10 mounted on the vertical movement unit 12.

Figure 6:
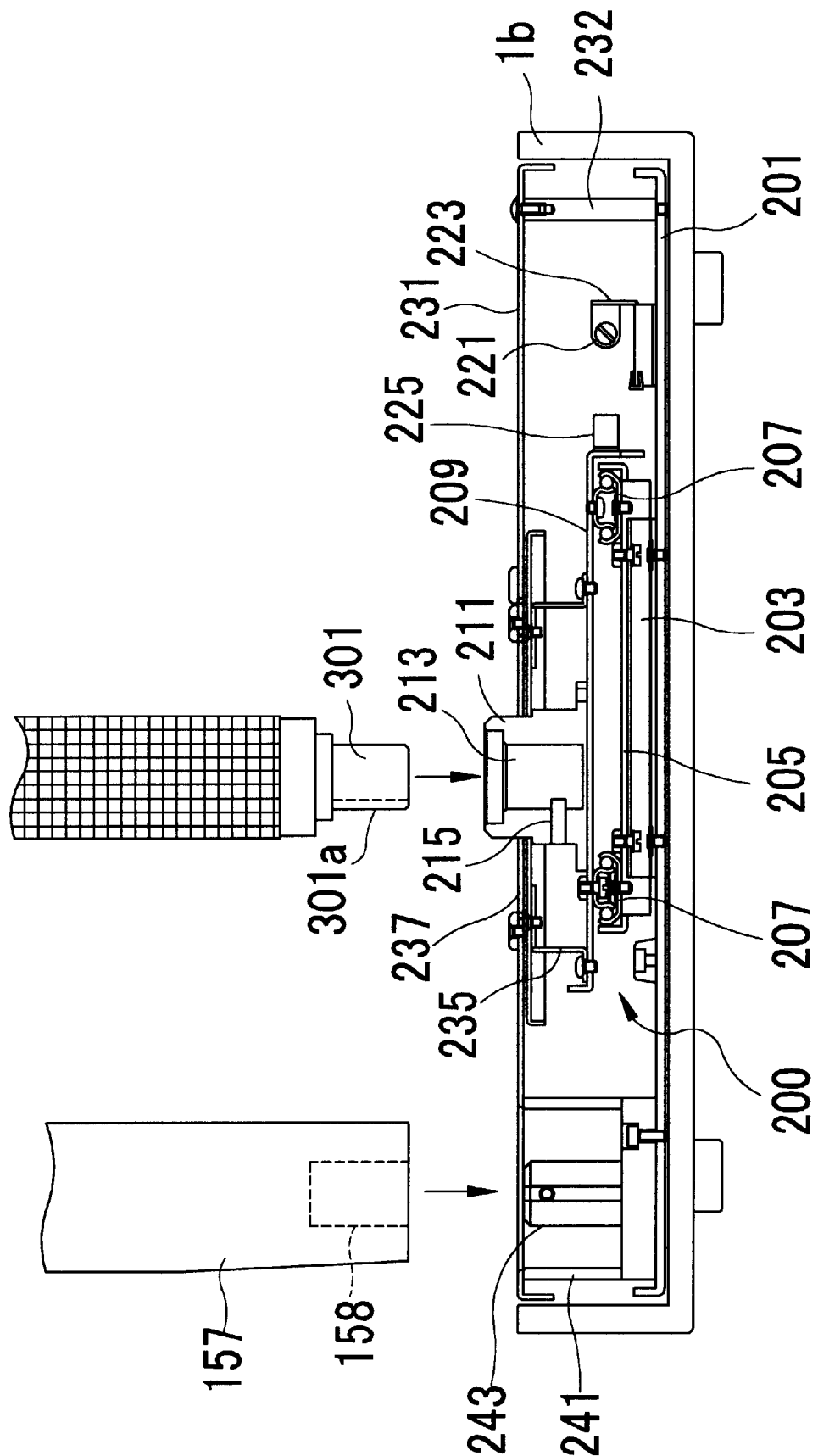
FIG. 6 is a sectional side view of a horizontal movement system, attachment systems of a head support unit and the vertical movement unit.
Figure 7:
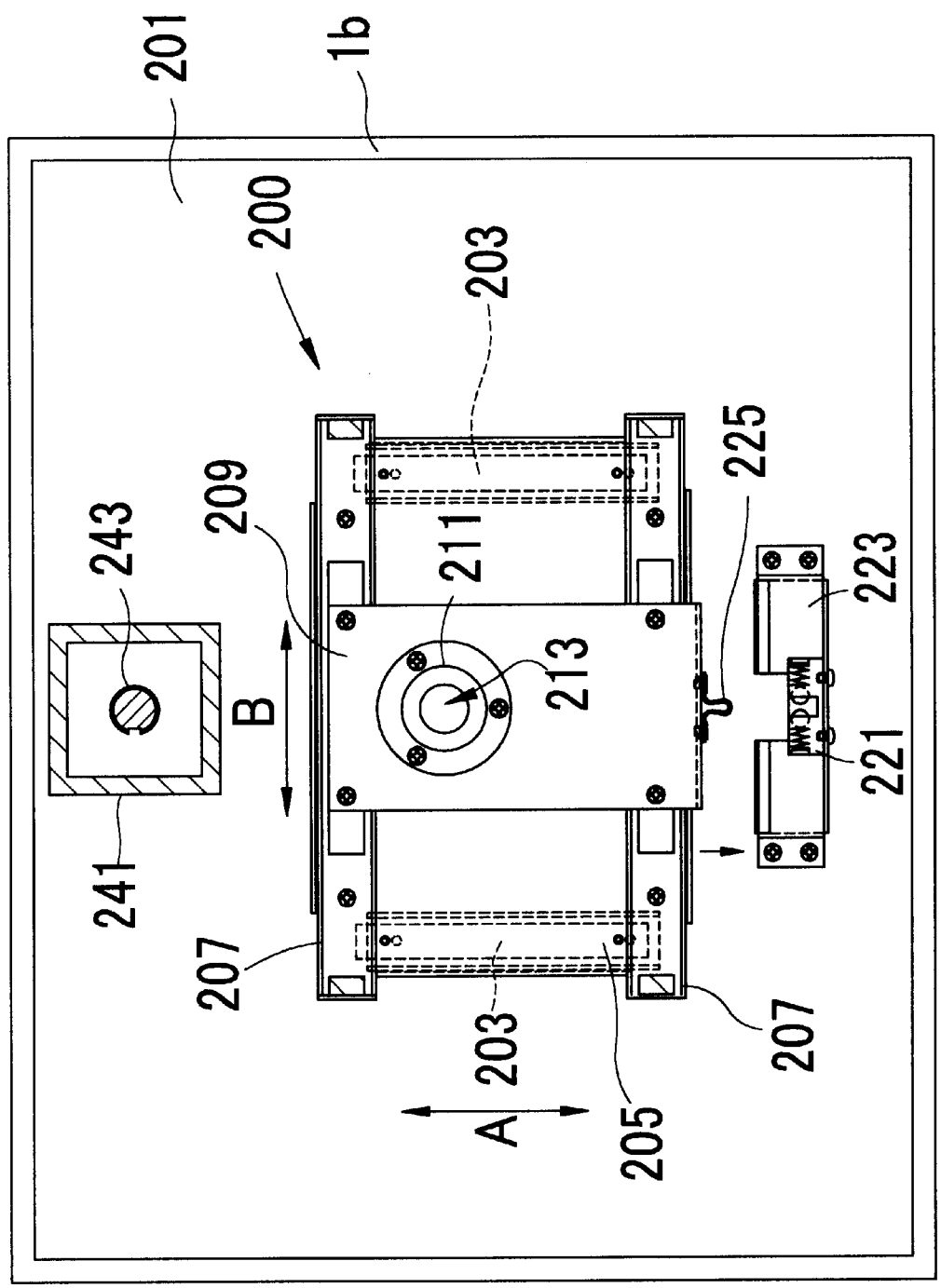
FIG. 7 is a plane view of the horizontal movement system, the attachment systems of the head support unit and the vertical movement unit.

On the upper side of the cover 1*b*, as shown in FIG. 6, an upper cover 231 for keeping the horizontal movement system 200 contained in the cover 1*b* from sight is fixed to the bottom plate 201 by means of a fixing member 232 and others. This upper cover 231 is provided with an opening 233 (see FIG. 1) in an area where the vertical movement unit 12 is horizontally moved. A slide cover 237 is fixed to the upper slidable plate 209 through a fixing plate 235. This slide cover 237 serves as a covering for the opening 233.

In the case cover 1b on the examinee side, formed is a block 241 having a square cavity for allowing attachment of the lower portion of the support base 157 to the cover 1b. An attachment shaft 243 is fixedly provided in the center of the cavity of the block 241. On the other hand, the support base 157 is formed, in the underside thereof, with a recess 158 engageable with the shaft 243. When the lower portion of the support base 157 is inserted in the cavity of the block 241 so that the recess 158 is engaged on the shaft 243, the head support unit 11 can be mounted on the cover 1b with a single motion.

At the time of carrying, the eye examination unit 10 and other separate units are housed in the corresponding spaces of the carrying case 1. On the other hand, at the time of executing eye examination (measurement) in a stable state in a group examination or an outside sale of spectacles, the cover 1b is assembled as a base of the eye examination unit 10 to be used as a stationary type. To be more specific, the cover 1b is put on a table or the like and then the head support unit 11 and the vertical movement unit 12 are assembled thereon as shown in FIGS. 3 and 4. The assembling of each unit can be made with a single motion as mentioned above without use of tools.

At the eye examination (measurement) time, the examiner requests the examinee to put his/her head on the head support 11 to make the position of the examinee's eye stable, and makes alignment of the eye examination unit 10 with respect to the examinee's eye. This alignment adjustment is performed in the manner that the examiner observes the image of the anterior part of the examinee's eye displayed on the monitor 101, the alignment target image, and an aiming mark, while operates the knob 303 to bring the alignment target image and the aiming mark into a predetermined relation. When the knob 303 is operated to move in the forward, backward, leftward, and rightward directions, the eye examination unit 10 mounted on the vertical movement unit 12 can be stably moved in the same directions by means of the horizontal movement system 200. When the knob 303 is operated to rotate, the eye examination 10 can be moved in the vertical direction.

Upon completion of alignment as above, the examiner pushes an eye examination (measurement) start switch on the operation section 106 to execute the eye examination (measurement). Alternatively, the eye examination unit 10 may judge the alignment state and automatically start the eye examination (measurement). Examination (measurement) data about the examinee's eye is transmitted to the station unit 13 through a connecting cable 20 (see FIG. 3) which connects the eye examination unit 10 to the station unit 13. A printer 13a in the station unit 13 then prints out examination (measurement) results. Electrical power is also supplied from the AC power source in the station unit 13 to the eye examination unit 10 through the cable 20. The data about the examined eye transmitted to the station unit 13 is further sent to an external computer or a subjective eye examination device by cable communications or optical communications. The above data transmission from the eye examination unit 10 to the station unit 13 may be conducted by optical communications. In this case, if the eye examination unit 10 is battery-operated, the need for the cable 20 may be eliminated.

After completion of the eye examination (measurement), the units are demounted from the cover 1b and housed in the spaces 4a–4c of the case body 1a and the space 4d of the center pad 5, respectively. The cover 1b is then closed to put the carrying case 1 into a portable state. It is to be noted that the protrusion 225 of the horizontal movement system 200 is held in engagement with the ball catch 221 during carrying of the case 1, thereby locking the movement of the holder 211.

Figure 8:
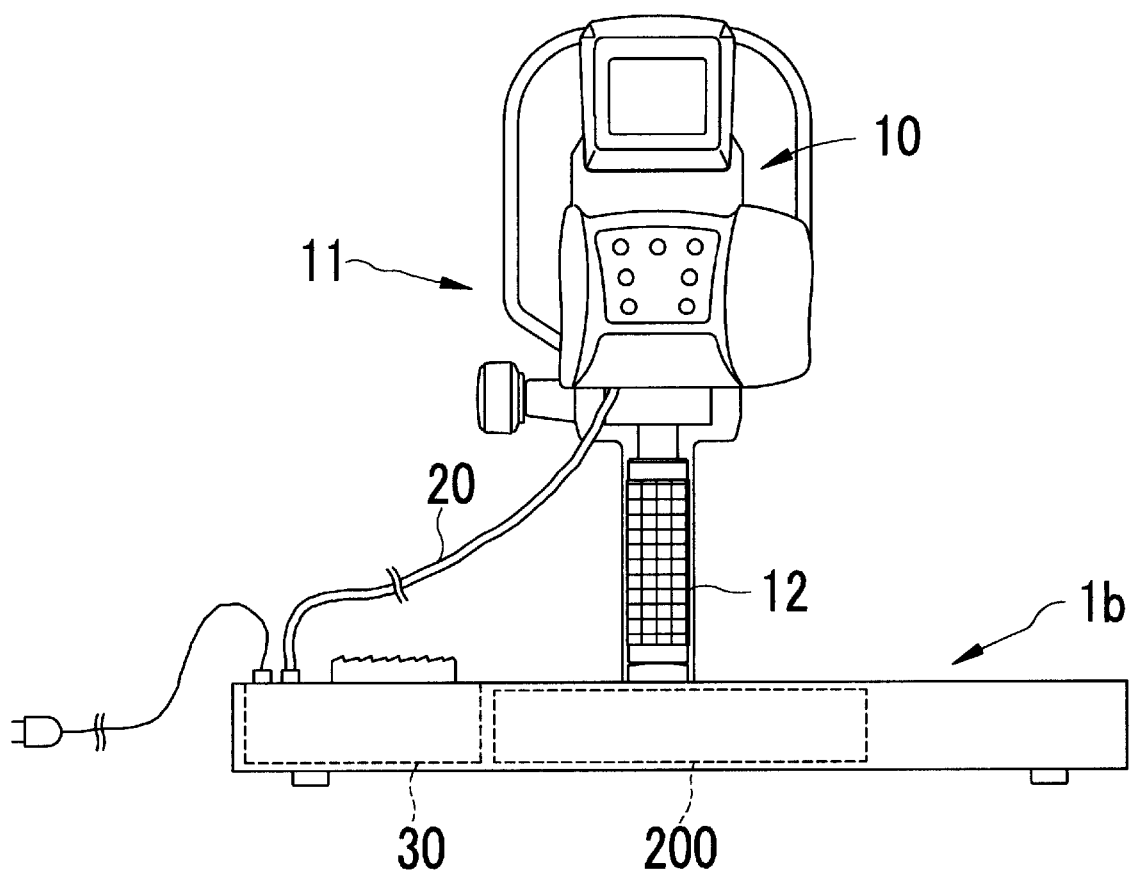
FIG. 8 is a front view of an eye examination device seen from an examiner side in another embodiment according to the present invention.

FIG. 8 is an eye examination device in another embodiment according to the present invention. In this embodiment, a unit 30 including a printer, an AC power source, and a communication section for transmitting data about an examined eye to an external device is integrally provided in the inside of a cover 1b. This makes it possible to reduce troublesomeness in preparing for use or housing for carry. Furthermore, the carrying case 1 can be made more compact with further reduced weight, and also the manufacturing cost can be reduced.

The present invention may be embodied in other specific forms without departing from the essential characteristics thereof. For instance, a part of the carrying case 1 is used as a base of the eye examination device in the above embodiments. Alternatively, the whole carrying case 1 may be used as the base. In addition, the above head support unit 11 and the vertical movement unit 12 may be configured to be foldable. This can simplify works for assembling and disassembling.

As described above, according to the present invention, the eye examination device enables stable eye examination (measurement) as a stationary type, providing improved operability. Furthermore, the eye examination device including the eye examination unit, its peripheral units, and the carrying case can be reduced in weight and size, improving its carryability.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto.

What is claimed is:

1. An eye examination device including:
    an eye examination unit for examining or measuring an eye of an examinee;
    a carrying case including a first housing part for housing the eye examination unit and a base part which mounts thereon the eye examination unit;
    a horizontal movement unit which moves the eye examination unit in a horizontal direction with respect to the base part; and
    a vertical movement unit which moves the eye examination unit in a vertical direction with respect to the base part.

2. The eye examination device according to claim 1, wherein the base part is integrally provided with the horizontal movement unit.

3. The eye examination device according to claim 1 further including a support unit which supports the examinee's eye in a stable position,
    wherein the carrying case further includes a second housing part for housing the support unit, and the base part includes a fixed support part which detachably supports the support unit.

4. The eye examination device according to claim 1, wherein the vertical movement unit includes an eye examination unit support part which detachably supports the eye examination unit, the base part includes a movable support part which detachably supports the vertical movement unit, and the horizontal movement unit moves the movable support part in a horizontal direction.

5. The eye examination device according to claim 1, wherein the base part is integrally provided with at least one of a printer part which prints measurement data obtained by the eye examination unit and a communication part which transmits the measurement data to an external device.

6. An eye examination device including:
   an eye examination unit for examining or measuring an eye of an examinee;
   a support unit which supports the examinee's eye in a stable position; and
   a carrying case including a first housing part for housing the eye examination unit and a second housing part for housing the support unit,
   the carrying case further including a base part provided with a movable support part which detachably supports the eye examination unit, a horizontal movement unit which moves the movable support part in a horizontal direction, and a fixed support part which detachably supports the support unit.

7. The eye examination device according to claim 6 further including a vertical movement unit which moves the eye examination unit in a vertical direction, wherein the movable support part supports the eye examination unit through the vertical movement unit.

8. The eye examination device according to claim 6, wherein the base part is integrally provided with at least one of a printer part which prints measurement data obtained by the eye examination unit and a communication part which transmits the measurement data to an external device.

9. A carrying case for housing an eye examination unit for examining or measuring an eye of an examinee, the carrying case including:
   a first housing part for housing the eye examination unit; and
   a base part provided with a movable support part which detachably supports the eye examination unit and a horizontal movement unit which moves the movable support part in a horizontal direction.

10. The carrying case according to claim 9 further including a second housing part for housing a support unit which supports the examinee's eye in a stable position,
    wherein the base part is provided with a fixed support part which detachably supports the support unit.

11. The carrying case according to claim 9, wherein the movable support part supports the eye examination unit through a vertical movement unit which moves the examination unit in a vertical direction.

12. The carrying case according to claim 9, wherein the base part is integrally provided with at least one of a printer part which prints measurement data obtained by the eye examination unit and a communication part which transmits the measurement data to an external device.

* * * * *